(12) United States Patent
Sekizawa et al.

(10) Patent No.: US 7,401,533 B2
(45) Date of Patent: Jul. 22, 2008

(54) DISSOLUTION TESTER

(75) Inventors: Kazutoshi Sekizawa, Hachioji (JP); Masao Yamazaki, Hachioji (JP)

(73) Assignee: JASCO Corporation, Hachioji-shi, Tokyo (JP)

( * ) Notice: Subject to any disclaimer, the term of this patent is extended or adjusted under 35 U.S.C. 154(b) by 274 days.

(21) Appl. No.: 11/383,572

(22) Filed: May 16, 2006

(65) Prior Publication Data
US 2006/0260421 A1  Nov. 23, 2006

(30) Foreign Application Priority Data
May 17, 2005  (JP) ............................. 2005-144172

(51) Int. Cl.
*G01N 33/15* (2006.01)
(52) U.S. Cl. ........................................................ 73/866
(58) Field of Classification Search ................... 73/866
See application file for complete search history.

(56) References Cited

U.S. PATENT DOCUMENTS 6,170,980 B1 * 1/2001 Martin ........................ 366/191
6,308,584 B1 * 10/2001 Benz ............................ 73/866
6,727,480 B2 * 4/2004 Fernando et al. ............ 219/549
7,024,955 B2 * 4/2006 Carlson et al. ................ 73/866
2005/0166688 A1 * 8/2005 Tian et al. ..................... 73/866

FOREIGN PATENT DOCUMENTS

JP          2000-283977          10/2000

* cited by examiner

*Primary Examiner*—Robert R Raevis
(74) *Attorney, Agent, or Firm*—Rankin, Hill & Clark LLP (57) ABSTRACT

A dissolution tester comprising: a constant-temperature-water tank; a vessel for introducing a dissolution test liquid; a vessel lid having a suction hole for sucking up the test liquid; a suction nozzle which can move up and down together with the nozzle holder; and an administration mechanism for automatically administering a sample for conducting a dissolution test into the vessel; the administration mechanism comprises an administration hole provided at the vessel lid; a sample receiver provided at the vessel lid, for holding the sample at the vessel lid when the administration hole is closed; and a manipulator rod which can move up and down together with the nozzle holder, for opening the administration hole by making contact with the sample receiver such that the sample on the sample receiver is made to fall into the vessel via the administration hole, when carrying out administration.

8 Claims, 5 Drawing Sheets

DISSOLUTION TESTER

RELATED APPLICATIONS

This application claims priority to the Japanese Patent Application 2005-144172 dated on May 17, 2005 and is hereby incorporated with reference for all purposes.

BACKGROUND OF THE INVENTION

1. Field of the Invention

The present invention relates to dissolution testers, and more particularly, to an improved stabilizing mechanism therefor.

2. Prior Art

Conventionally, in order to ensure consistent quality of drug samples, dissolution tests are conducted to test the dissolution of compounds of interest from those samples.

Various different kinds of dissolution testers have been developed for conducting such tests. For example, one such dissolution tester in the related art is the device described in Japanese Unexamined Patent Application Publication No. 2000-283977.

Dissolution testers generally include a vessel, a paddle (or a rotating basket), a rotary shaft, an electric motor, and a constant-temperature-water tank.

In a dissolution test, a typical sequence of operations carried out with the dissolution tester is as follows. A fixed amount of test liquid is placed in the vessel and the temperature of the test liquid in the vessel is maintained at 37±5° C. Then, after immersing a sample to the center at the bottom of the vessel, the paddle is rotated at a specified position. The test liquid is then collected from the vessel after a specified period of time; this is known as the sample solution. The compounds of interest in the sample solution are then measured using a specified method, and a dissolution rate corresponding to the indicated amount is obtained.

It is essential to ensure stability of the dissolution test.

However, in dissolution testers using conventional techniques, it is difficult to further stabilize the dissolution test. In addition, the factors preventing further stabilization of the dissolution test with the conventional techniques are not well known.

SUMMARY OF THE INVENTION

The present invention has been conceived in light of the above-described problems in the related art. An object thereof is to provide a dissolution tester that can conduct a dissolution test more stably.

As a result of extensive investigation of the problems described above, the inventors of the present invention found that, in order to further stabilize the dissolution test, it is extremely important to make the dissolution time uniform among a plurality of vessels set in a single dissolution tester.

In practice, however, it is extremely difficult to make the dissolution times uniform across a plurality of vessels, and the inventors observed the phenomenon described below.

Administration is normally carried out manually by administering one tablet to each vessel in turn. Therefore, there is some variation in the administration time from vessel to vessel; on the other hand, the test liquid is sucked up from the vessels simultaneously using suction nozzles.

Accordingly, in the conventional method, there are differences in the dissolution times, that is, the time from administration to suction, among the plurality of vessels, even in a single dissolution tester. Therefore, there are also differences in the dissolution rates among the vessels, and the inventors found that it is sometimes not possible to conduct a stable dissolution test.

Based on this knowledge, the inventors extensively investigated ways to solve this problem and found that providing a large, specially designed administration mechanism merely for simplifying the administration procedure is an expensive approach. Furthermore, providing such a specially designed administration mechanism may, in itself, cause additional problems that prevent a stable dissolution test. Therefore, this approach is not employed in the present invention for solving the problem described above.

In contrast, in order to carry out simultaneous administration for a plurality of vessels using a low-cost, simple configuration in the present invention, it is extremely important to construct an automatic simultaneous-administration mechanism described below by aggressively using standard components of the dissolution tester. This approach was used to realize the present invention.

In order to achieve the object described above, a dissolution tester according to the present invention includes a constant-temperature-water tank, a vessel, a vessel lid, a nozzle holder, a suction nozzle, and an administration mechanism. The administration mechanism comprises an administration hole, a sample receiver, and a manipulator rod.

The constant-temperature-water tank contains constant-temperature water.

The vessel comprises a main body having a bottom and a top opening for introducing a dissolution test liquid. A desired portion of the main body is immersed in the constant-temperature water inside the constant-temperature-water tank.

The vessel lid is disposed at the top opening of the vessel. The vessel lid has a suction hole for sucking up the test liquid.

The nozzle holder is disposed above the vessel lid. The nozzle holder can move up and down.

The suction nozzle is suspended from the nozzle holder. The suction nozzle can move up and down together with the nozzle holder. The suction nozzle sucks up the test liquid inside the vessel when the suction nozzle is inserted through the suction hole in the vessel lid.

The administration mechanism automatically administers a sample for conducting a dissolution test into the vessel at a predetermined timing.

The administration hole is provided at the vessel lid. The administration hole introduces the sample into the vessel.

The sample receiver is provided at the vessel lid, freely opens and closes the administration hole. The sample receiver holds the sample at the vessel lid when the administration hole is closed. The sample receiver administers the sample into the vessel via the administration hole when the administration hole is open.

The manipulator rod is provided at the nozzle holder. The manipulator rod opens the administration hole by making contact with the sample receiver when carrying out administration.

In the present invention, when carrying out administration, by lowering the manipulator rod together with the nozzle holder to make the manipulator rod contact the sample receiver and to push the sample receiver open in the downward direction with the manipulator rod, the administration hole is opened. Thus, the sample, which is set in advance on the sample receiver, is made to fall into the vessel via the administration hole.

<Sample Receiver>

It is preferable in the present invention that the sample receiver comprises: a door, a rod-contacting member and a support member.

The door can rotate in a hinged manner at the administration hole of the vessel lid and on which the sample is mounted.

The rod-contacting member contacts the manipulator rod and rotates together with the door.

The support member supports the door in a hinged manner to enable rotation of the door relative to the vessel lid.

In the present invention, when the rod-contacting member is pushed downward by the manipulator rod, the door rotates together with the rod-contacting member to open the administration hole. Thus, the sample, which is set on the door in advance, is made to fall into the vessel via the administration hole.

<Manipulator Rod>

In the present invention, the length of the manipulator rod from the nozzle holder is shorter than the length of the suction nozzle. The length of the manipulator rod is preferably such that when carrying out administration, the manipulator rod makes contact with the sample receiver to open the administration hole, and the suction nozzle is located at a position in the vertical direction where the suction nozzle does not make contact with the bottom of the vessel. And the length of the manipulator rod is preferably such that when sucking up the test liquid, the manipulator rod does not make contact with the sample receiver to close the administration hole, and the suction nozzle is located at a vertical position allowing suction of the test liquid inside the vessel.

<Basket>

It is preferable in the present invention to provide a basket.

The basket contains the sample, the basket is placed on the sample receiver.

It is preferable in the present invention that when carrying out administration, the sample is made to drop into the vessel via the administration hole together with the basket.

Effect

Providing a dissolution tester according to the present invention with an administration mechanism allows administration to be carried out more reliably at a predetermined timing using a simple configuration. Therefore, it is possible to conduct a stable dissolution test with the simple configuration.

Providing a sample receiver in the present invention with a door and a spring allows administration to be carried out more reliably. Therefore, it is possible to conduct the dissolution test more stably.

Regulating the length of manipulator rods from a nozzle holder in the present invention allows administration to be carried out more reliably. Therefore, it is possible to conduct the dissolution test more stably.

Providing a basket in the present invention allows administration to be carried out more reliably, using a simple configuration. Therefore, it is possible to conduct the dissolution test more stably.

DESCRIPTION OF THE PREFERRED EMBODIMENT

A preferred embodiment of the present invention will be described below based on the drawings.

Figure 1:
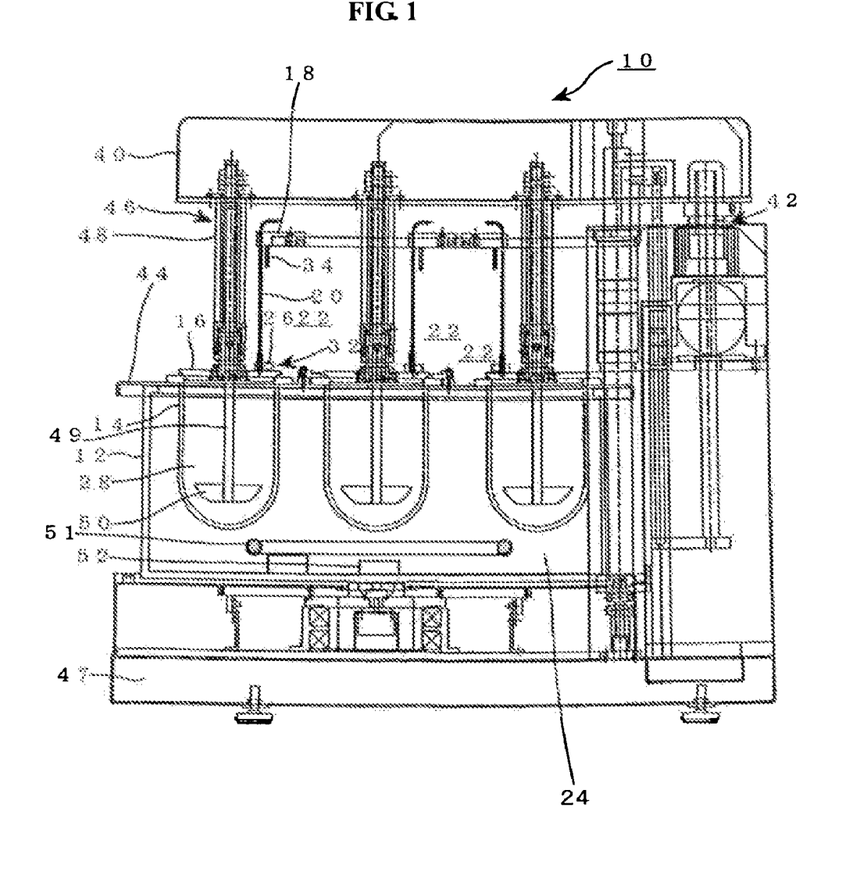
FIG. 1 is a diagram showing an outline configuration of a dissolution tester according to an embodiment of the present invention.

FIG. 1 is a side view of A dissolution tester 10 according to the embodiment of the present invention.

Figure 2:
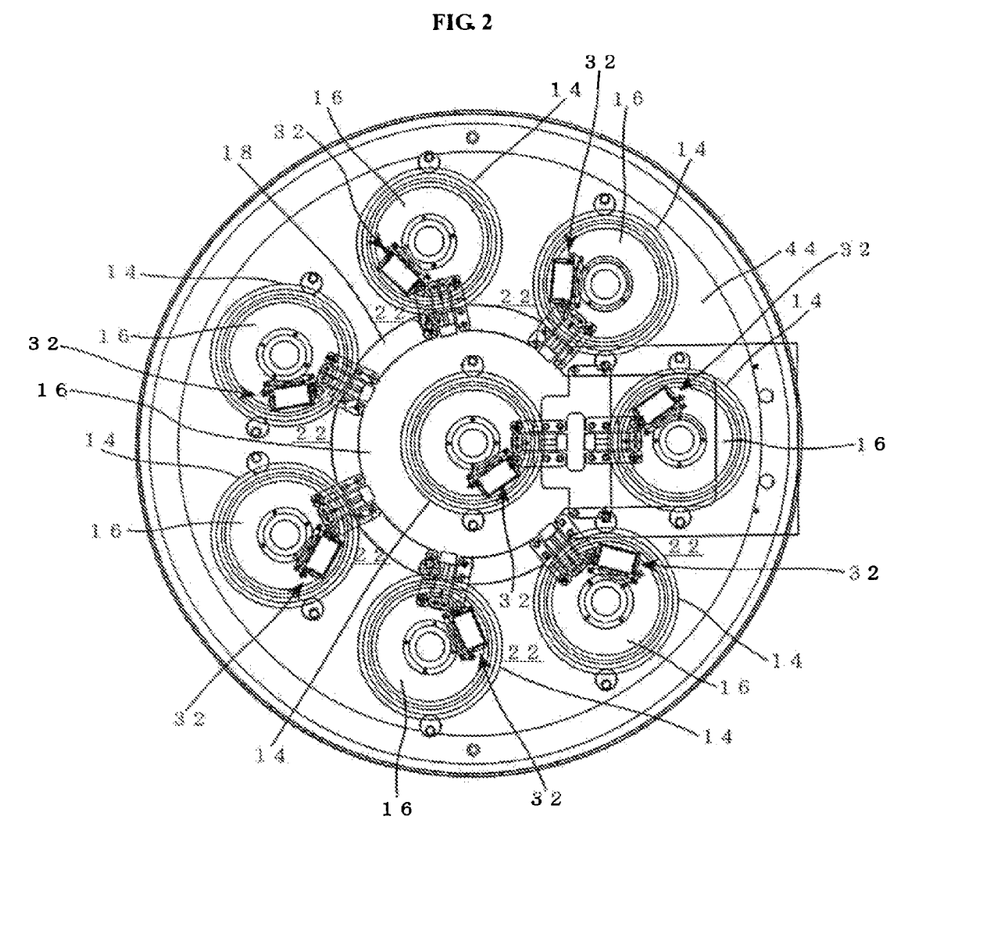
FIG. 2 is a top view of vessel lids in the dissolution tester according to this embodiment.

FIG. 2 shows the dissolution tester 10 according to this embodiment, as viewed from a location above vessel lids 16.

In this embodiment, the dissolution tester 10 includes a constant-temperature-water tank 12, vessels 14, the vessel lids 16, a nozzle holder 18, suction nozzles 20, and automatic simultaneous-administration mechanisms (administration mechanisms) 22.

The constant-temperature-water tank 12 has a circular cross section and contains constant-temperature water 24.

The vessels 14 have circular cross sections. Samples 26 and test liquids 28 are placed in the vessels 14, and desired portions of the vessels 14 are immersed in the constant-temperature water 24 in the constant-temperature-water tank 12.

The vessel lids 16 have circular cross sections. The vessel lids 16 are disposed at openings at the top of the vessels 14 and have suction holes 29 for sucking out the test liquids 28. The vessel lids 16 each have a tapered portion whose outer diameter at the bottom surface thereof is smaller than the outer diameter at the top surface thereof.

The nozzle holder 18 moves up and down above the vessel lids 16.

The suction nozzles 20 are suspended from the nozzle holder 18 and can move up and down together with the nozzle holder 18. When the suction nozzles 20 are inserted through the suction holes 29 in the vessel lid 16, they suck out the test liquids 28 inside the vessels 14.

The automatic simultaneous-administration mechanisms 22, which are a characterizing feature of this embodiment, each include an administration hole 30, a sample receiver 32, and a manipulator rod 34. The automatic simultaneous-administration mechanisms 22 automatically administer the samples 26 to the vessels 14 at a predetermined timing.

The administration holes 30 are provided for the vessel lids 16 and are used for introducing the samples 26 into the vessels 14.

The sample receivers 32 can open and close the administration holes 30 in the vessel lids 16. When the administration holes 30 are closed, the sample receivers 32 hold the samples 26 in the vessel lids 16. When the administration holes 30 are opened, the sample receivers 32 administer the samples 26 into the vessels 14 via the administration holes 30.

The manipulator rods 34 are provided on the nozzle holder 18. During administration, the manipulator rods 34 make contact with the sample receivers 32 to open the administration holes 30.

In this embodiment, during administration, the manipulator rods 34 are lowered together with the nozzle holder 18 until they contact the sample receivers 32, whereupon the sample receivers 32 are pushed open in the downward direction by the manipulator rods 34 to open the administration holes 30. Therefore, the samples 26 which were set in advance in the sample receivers 32 automatically drop into the vessels 14 via the administration holes 30.

<Dissolution Tester>

The dissolution tester 10 of this embodiment also includes a head 40, a support arm 42, a tank lid 44, and lid-moving shafts 46.

The head 40 is disposed above the constant-temperature-water tank 12 and moves up and down relative to a base 47. The nozzle holder 18 is lowered together with the head 40, until it reaches a specified position in the vertical direction. At a position below this specified vertical position, the nozzle holder 18 moves up and down independently of the head 40.

The support arm 42 supports the head 40 in a cantilevered fashion so that it can move up and down relative to the base 47.

The tank lid 44 is disposed at an opening at the top of the constant-temperature-water tank 12. The tank lid 44 is provided with retaining holes having inner diameters slightly larger than the outer diameters of main bodies of the vessels 14 and slightly smaller than the outer diameters of outwardly protruding flanges of the vessels 14. By catching the protruding flanges of the vessels 14 in these retaining holes, the tank lid 44 holds the vessels 14 so that desired portions thereof are immersed in the constant-temperature water in the constant-temperature-water tank 12.

The lid-moving shafts 46 are suspended from the bottom of the head 40, are aligned with and secured to the centers of the vessel lids 16, and move up and down together with the head 40. Each lid-moving shaft 46 includes a tube 48 and a rotary shaft 49, and a paddle 50 is provided at the bottom of the rotary shaft 49.

The constant-temperature-water tank 12 includes a circular heater 51 formed in the shape of a circle at the bottom inside the circular constant-temperature-water tank 12 such that the center axis of the constant-temperature-water tank 12 and the center axis of the circular heater 51 are aligned, and a constant-temperature-water agitator 52, such as a paddle, disposed at the center at the bottom inside the circular constant-temperature-water tank 12.

Constructing the dissolution tester 10 of this embodiment in this way allows a stable dissolution test to be conducted.

In order to conduct a stable dissolution test, the inventors of the present invention found that it is extremely important to introduce the samples into the plurality of vessels 14 simultaneously, using a simple, low-cost configuration.

Administration is also carried out in conventional dissolution testers, but it is normally performed manually.

However, this type of manual procedure is complex and time consuming. In addition, samples are introduced into the plurality of vessels 14 with some time differences. Therefore, because there are variations in the dissolution times among the plurality of vessels 14 when using a conventional technique, it may not be possible to conduct the dissolution test with high accuracy.

Providing large, specially designed equipment for simplifying the administration procedure is expensive. Also, providing such large, specially designed equipment may itself introduce additional factors causing instability in the dissolution test.

In contrast, in the dissolution tester 10 according to this embodiment, in order to simultaneously introduce the samples 26 into the plurality of vessels 14 using a simple, low-cost configuration, it is extremely important to construct an automatic simultaneous-administration mechanism by making aggressive use of some of the standard components in the dissolution tester 10.

More specifically, in the dissolution tester 10 in this embodiment, the manipulator rods 34 are provided in the raising and lowering mechanism for the suction nozzles 20.

The vessel lids 16 are provided in the dissolution tester 10 mainly for preventing evaporation of the test liquids 28, and the sample receivers 32 are also provided on these vessel lids 16.

By constructing the automatic simultaneous-administration mechanism in this way by making aggressive use of standard components of the dissolution tester 10, the configuration for carrying out automatic simultaneous administration can be simplified and the costs can be reduced.

The automatic simultaneous-administration mechanism of this embodiment is described in more detail below.

Figure 3A:
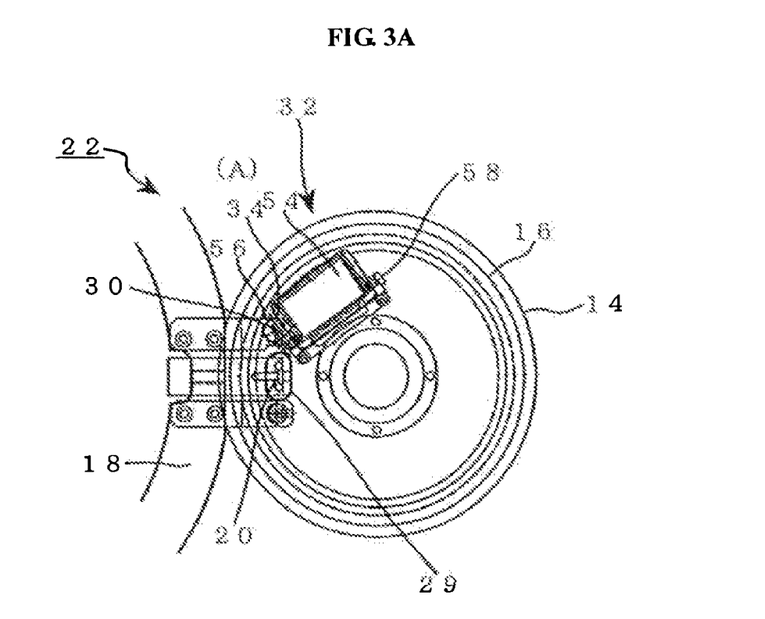
FIGS. 3A and 3B are diagrams showing an outline configuration of an automatic simultaneous-administration mechanism, which is a characterizing feature of the dissolution tester shown in FIG. 1.
Figure 3B:
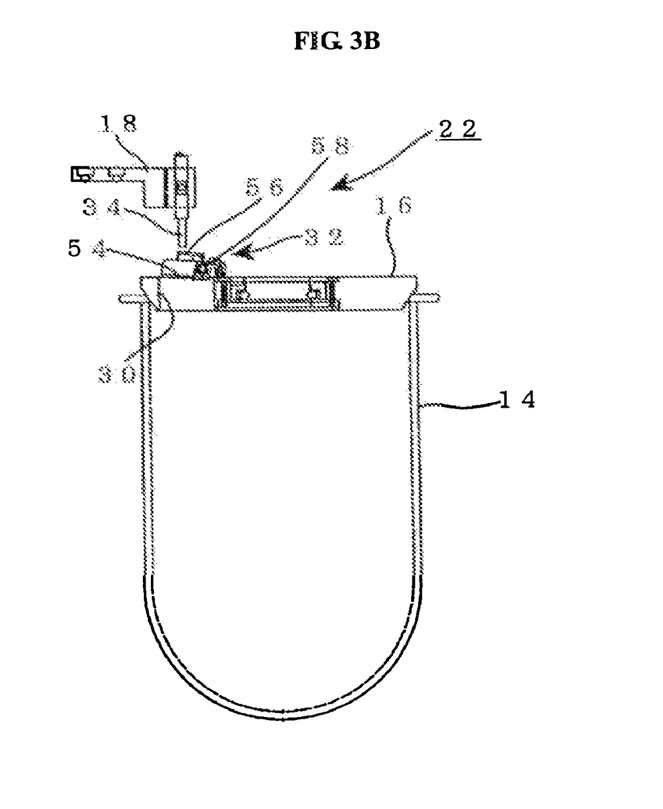

The essential parts of the automatic simultaneous-administration mechanism of this embodiment are shown in magnified form in FIGS. 3A and 3B. FIG. 3A shows a vicinity of the automatic simultaneous-administration mechanism as viewed from above, and FIG. 3B shows the vicinity of the automatic simultaneous-administration mechanism as viewed from a side.

<Sample Receivers>

The sample receivers 32 in this embodiment each include a door 54, a rod-contacting member 56, and a door-supporting member 58.

When the sample 26 is provided on the sample receiver 32, the door 54 can rotate like a hinge with the door-supporting member 58 being used as a shaft.

The rod-contacting member 56 is provided on the door 54, and when it makes contact with the manipulator rod 34, it rotates together with the door 54.

The door-supporting member 58 includes a spring and supports the door 54 so that it can rotate in a hinged manner relative to the vessel lid 16.

Therefore, when carrying out administration, the rod-contacting member 56 is pushed downward by the manipulator rod 34 to open the door 54 and thus open the administration hole 30. Then, the sample 26 which was previously placed on the door 54 automatically falls into the vessel 14 through the administration hole 30.

<Manipulator Rods>

In this embodiment, the lengths of the manipulator rods 34 from the nozzle holder 18 are shorter than the lengths of the suction nozzles 20. When carrying out administration in this embodiment, the manipulator rods 34 make contact with the sample receivers 32 to open the administration holes 30, and the suction nozzles 20 are located at a vertical position inside the vessels 14 where they do not make contact with the bottoms of the vessels 14. When sucking out the test liquids 28, the manipulator rods 34 are removed from the sample receivers 32 to close the administration holes 30, and the suction nozzles 20 are located at a vertical position where they can suck out the test liquids 28 at a desired depth inside the vessels 14. It is preferred that the lengths of the manipulator rods from the nozzle holder 18 be determined in this way.

Figures 4A, 4B, 4C:
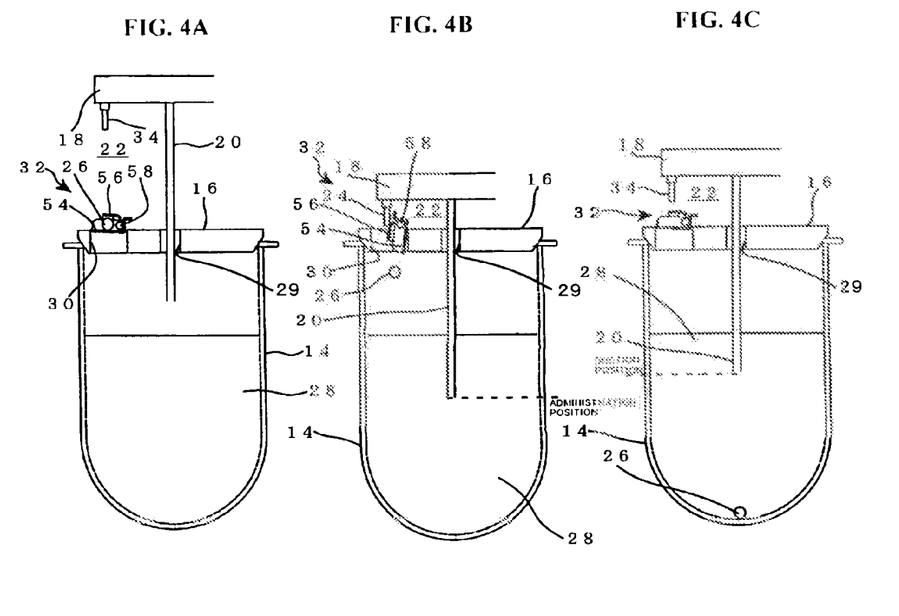
FIGS. 4A to 4C are diagrams showing the operation of the automatic simultaneous-administration mechanism shown in FIG. 3.

Using this type of automatic simultaneous-administration mechanism, administration is carried out as shown in FIGS. 4A to 4C. FIG. 4A shows a state before beginning the dissolution test, FIG. 4B shows a state during administration of the sample 26 (when starting the dissolution test), and FIG. 4C shows a state when sucking up the test liquid 28.

<Prior to Test Commencement>

As shown in FIG. 4A, prior to commencing the dissolution test, the suction nozzle 20 and the manipulator rod 34 are located above the vessel 14. The sample 26 is placed on the door 54 in advance.

<Test Commencement>

As shown in FIG. 4B, when carrying out administration, the suction nozzle 20 is lowered to an administration position, which is lower than a standard suction position. When the manipulator rod 34 makes contact with the rod-contacting member 56 to open the door 54, the administration hole 30 is opened. Therefore, the sample 26 falls from the door 54 into the vessel 14 via the administration hole 30. Thus, the dissolution test starts simultaneously with administration.

After the sample 26 falls into the vessel 14, when the manipulator rod 34 is raised together with the suction nozzle 20, the manipulator rod 34 is separated from the rod-contacting member 56. Therefore, the door 54 is closed by the force of the door-supporting member 58 (that is, the elastic force of the spring), and the administration hole 30 is closed. Therefore, it is possible to reliably prevent evaporation of the test liquid 28 inside the vessel 14.

<Test-Liquid Suction>

When sucking up the test liquid after a specified period of time has passed from commencement of the dissolution test, the suction nozzle 20 is lowered to the standard suction position shown in FIG. 4C. The suction nozzle 20 then sucks up the test liquid 28 inside the vessel 14.

After this administration, when sucking up the test liquid 28, and obviously during the dissolution test itself, the manipulator rod 34 does not reach the sample receiver 32 in the vessel lid 16 and so does not push down the sample receiver 32. The administration hole 30 thus remains closed. In this embodiment, therefore, it is possible to reliably prevent evaporation of the test liquid 28 inside the vessel 14.

A dissolution rate is determined at a later stage by using the sucked-up test liquid 28 as a standard solution.

In the dissolution tester 10 according to this embodiment, constructing the automatic simultaneous-administration mechanism by aggressively using standard components of the dissolution tester allows the costs to be kept down and the configuration to be simplified. In addition, it is possible to simultaneously introduce samples 26 into a plurality of vessels 14 automatically.

Therefore, with this embodiment, it is possible to conduct a stable dissolution test using a simple configuration.

<Determination of Administration Timing>

This embodiment enables the dissolution test to be carried out more stably, even under the following conditions, using a simple configuration.

Specifically, if it is not possible to accurately determine the timing at which the samples 26 are introduced, even if introduced simultaneously, it is difficult to ensure a specified dissolution time.

In this embodiment, therefore, it is also extremely important to accurately determine the timing at which samples 26 are introduced.

When manually operating a specially designed administration mechanism, it is difficult to determine the timing at which the samples 26 are introduced using a computer (PC) or dissolution tester (DT). Therefore, in the conventional method, it is difficult to properly control the dissolution time from the point when the samples are introduced. Therefore, with the conventional method, it is difficult to conduct a stable dissolution test for a specified dissolution time.

In contrast, in this embodiment, the suction nozzles 20 are lowered to the position where the samples 26 were dropped under the control of a computer (PC) or dissolution tester (DT). Therefore, the timing at which the tablets (samples 26) are dropped can be automatically determined as being the time at which the measurement program starts. Therefore, the dissolution time from when the samples 26 are introduced can be controlled extremely accurately based on the timing at which the tablets (samples 26) are dropped. It is therefore possible to conduct a stable dissolution test for a specified dissolution time.

<Basket>

In order to make the administration more practical, it is preferable to use an approach described below in this embodiment.

Figure 5:
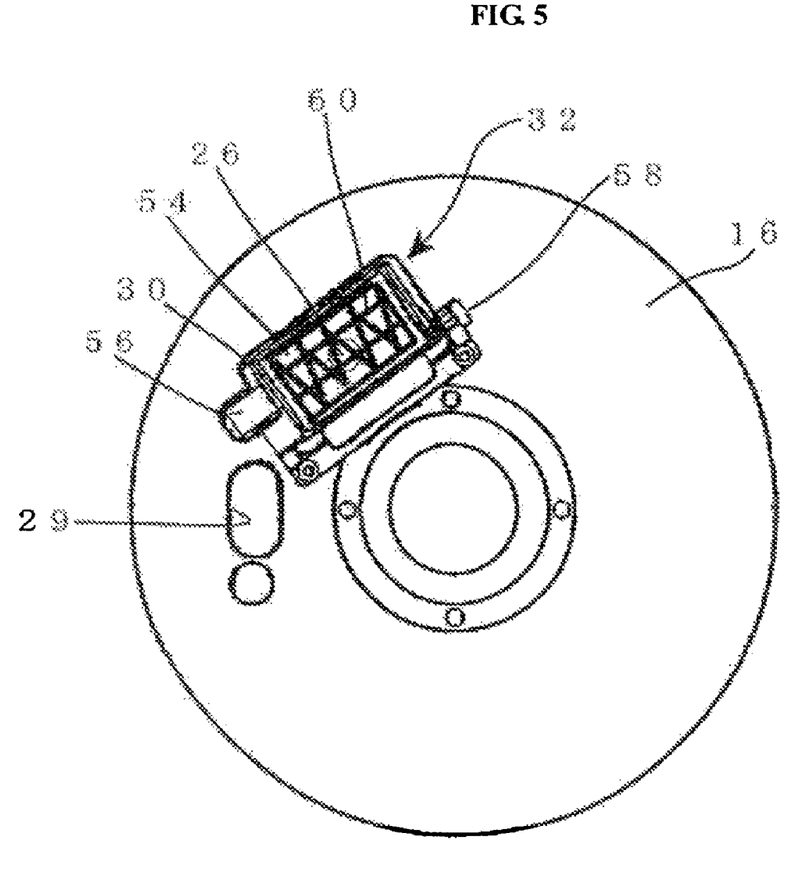
FIG. 5 is a diagram of a basket preferably used with the automatic simultaneous-administration mechanism shown in FIG. 3.

As shown in FIG. 5, a cylindrical mesh basket 60 is provided in this embodiment.

The sample 26 is placed in the basket 60 in advance, and the basket 60 is set on the sample receiver 32.

Then, when the sample receiver 32 is opened, the sample 26 falls into the vessel 14 together with the basket 60. This occurs in an identical manner for each of the vessels 14.

As a result, compared with the method where the sample 26 is directly administered, it is possible to make the administration timing more uniform across the vessels 14. With this embodiment, therefore, it is possible to carry out the dissolution test more stably for a plurality of vessels 14.

<Dosage Form>

The above configurations have been illustrated by using tablets as the dosage form of the samples 26. However, the present invention is not limited to tablets, and it is possible to use other dosage forms. Specifically, the present invention can be applied to capsules, granules, powder, and so forth.

What is claimed is:

1. A dissolution tester comprising:

a constant-temperature-water tank containing constant-temperature water;

a vessel comprising a main body having a bottom and a top opening for introducing a dissolution test liquid, a desired portion of the main body being immersed in the constant-temperature water inside the constant-temperature-water tank;

a vessel lid disposed at the top opening of the vessel and having a suction hole for sucking up the test liquid;

a nozzle holder which is disposed above the vessel lid and which can move up and down;

a suction nozzle which is suspended from the nozzle holder, which can move up and down together with the nozzle holder, and which sucks up the test liquid inside the vessel when inserted through the suction hole in the vessel lid; and an administration mechanism for automatically administering a sample for conducting a dissolution test into the vessel at a predetermined timing, wherein the administration mechanism comprises an administration hole provided at the vessel lid, for introducing the sample into the vessel;

a sample receiver provided at the vessel lid, for freely opening and closing the administration hole, for holding the sample at the vessel lid when the administration hole is closed, and for administering the sample into the vessel via the administration hole when the administration hole is open; and a manipulator rod provided at the nozzle holder, for opening the administration hole by making contact with the sample receiver when carrying out administration, and wherein, when carrying out administration, by lowering the manipulator rod together with the nozzle holder to make the manipulator rod contact the sample receiver and to push the sample receiver open in the downward direction with the manipulator rod, the administration hole is opened, and the sample, which is set in advance on the sample receiver, is made to fall into the vessel via the administration hole.

2. A dissolution tester according to claim 1, wherein the sample receiver comprises:
- a door which can rotate in a hinged manner at the administration hole of the vessel lid and on which the sample is mounted;
- a rod-contacting member which contacts the manipulator rod and rotates together with the door; and
- a support member for supporting the door in a hinged manner to enable rotation of the door relative to the vessel lid, and
- when the rod-contacting member is pushed downward by the manipulator rod, the door rotates together with the rod-contacting member to open the administration hole, and the sample, which is set on the door in advance, is made to fall into the vessel via the administration hole.

3. A dissolution tester according to claim 1, wherein the length of the manipulator rod from the nozzle holder is shorter than the length of the suction nozzle,
- the length of the manipulator rod being such that
- when carrying out administration, the manipulator rod makes contact with the sample receiver to open the administration hole, and the suction nozzle is located at a position in the vertical direction where the suction nozzle does not make contact with the bottom of the vessel, and
- when sucking up the test liquid, the manipulator rod does not make contact with the sample receiver to close the administration hole, and the suction nozzle is located at a vertical position allowing suction of the test liquid inside the vessel.

4. A dissolution tester according to claim 2, wherein the length of the manipulator rod from the nozzle holder is shorter than the length of the suction nozzle,
- the length of the manipulator rod being such that
- when carrying out administration, the manipulator rod makes contact with the sample receiver to open the administration hole, and the suction nozzle is located at a position in the vertical direction where the suction nozzle does not make contact with the bottom of the vessel, and
- when sucking up the test liquid, the manipulator rod does not make contact with the sample receiver to close the administration hole, and the suction nozzle is located at a vertical position allowing suction of the test liquid inside the vessel.

5. A dissolution tester according to claim 1, further comprising:
- a basket, containing the sample, which is placed on the sample receiver, wherein, when carrying out administration, the sample is made to drop into the vessel via the administration hole together with the basket.

6. A dissolution tester according to claim 2, further comprising:
- a basket, containing the sample, which is placed on the sample receiver, wherein, when carrying out administration, the sample is made to drop into the vessel via the administration hole together with the basket.

7. A dissolution tester according to claim 3, further comprising:
- a basket, containing the sample, which is placed on the sample receiver, wherein, when carrying out administration, the sample is made to drop into the vessel via the administration hole together with the basket.

8. A dissolution tester according to claim 4, further comprising:
- a basket, containing the sample, which is placed on the sample receiver, wherein, when carrying out administration, the sample is made to drop into the vessel via the administration hole together with the basket.

* * * * *